(12) United States Patent
Wiesmann et al.

(10) Patent No.: US 6,606,993 B1
(45) Date of Patent: *Aug. 19, 2003

(54) INTEGRATED PHYSIOLOGIC SENSOR SYSTEM

(75) Inventors: William Paul Wiesmann, Bethesda, MD (US); Loland Alexander Pranger, Montgomery Village, MD (US); Mary Sandra Bogucki, Branford, CT (US)

(73) Assignee: Bioasyst, Germantown, MD (US)

( * ) Notice: Subject to any disclaimer, the term of this patent is extended or adjusted under 35 U.S.C. 154(b) by 35 days.

This patent is subject to a terminal disclaimer.

(21) Appl. No.: 09/759,095

(22) Filed: Jan. 12, 2001

Related U.S. Application Data

(62) Division of application No. 09/134,483, filed on Aug. 14, 1998, now Pat. No. 6,199,550.

(51) Int. Cl.⁷ .......................... A61M 16/00; A62B 7/00; F16K 31/02
(52) U.S. Cl. .......................... 128/204.23; 128/202.22; 128/205.23; 128/206.21; 128/206.24; 128/206.26; 128/903; 340/573.1
(58) Field of Search .................. 128/201.19, 201.27, 128/202.13, 202.22, 204.23, 205.22, 205.25, 206.21, 903; 340/573, 573.1, 573.4, 573.6

(56) References Cited

U.S. PATENT DOCUMENTS

| | | | | |
|---|---|---|---|---|
| 4,016,876 A | * | 4/1977 | Martin et al. | 128/205.23 |
| 4,800,885 A | * | 1/1989 | Johnson | 600/532 |
| 4,846,183 A | * | 7/1989 | Martin | 600/532 |
| H1039 H | * | 4/1992 | Tripp, Jr. et al. | 128/206.28 |
| 5,157,378 A | * | 10/1992 | Stumberg et al. | 340/521 |
| 5,246,002 A | * | 9/1993 | Prosser | 600/532 |
| 5,285,782 A | * | 2/1994 | Prosser | 600/532 |
| 5,301,668 A | * | 4/1994 | Hales | 128/205.23 |
| 5,461,390 A | * | 10/1995 | Hoshen | 342/419 |
| 5,601,078 A | * | 2/1997 | Schaller et al. | 128/205.23 |
| 5,652,570 A | * | 7/1997 | Lepkofker | 340/573 |
| 5,731,757 A | * | 3/1998 | Layson, Jr. | 340/573 |
| 5,857,460 A | * | 1/1999 | Popitz | 128/206.21 |
| 5,867,103 A | * | 2/1999 | Taylor, Jr. | 340/573 |
| 5,990,793 A | * | 11/1999 | Bieback | 340/573.1 |
| 6,054,928 A | * | 4/2000 | Lemelson et al. | 340/573.4 |
| 6,100,806 A | * | 8/2000 | Gaukel | 340/573.4 |
| 6,160,481 A | * | 12/2000 | Taylor, Jr. | 340/573.4 |
| 6,199,550 B1 | * | 3/2001 | Wiesmann et al. | 128/204.23 |
| 6,201,475 B1 | * | 3/2001 | Stumberg et al. | 340/573.1 |
| 6,218,945 B1 | * | 4/2001 | Taylor, Jr. | 340/573.1 |
| 6,310,552 B1 | * | 10/2001 | Stumberg et al. | 340/573.1 |

* cited by examiner

*Primary Examiner*—Weilun Lo
*Assistant Examiner*—Joseph F. Weiss, Jr.
(74) *Attorney, Agent, or Firm*—Blaney Harper; Jones Day

(57) ABSTRACT

An embodiment of the present invention comprises a system for monitoring the physiologic status of a plurality of individuals wearing a self-contained breathing apparatus (SCBA) mask. Each SCBA mask incorporates a series of physiologic sensors that monitor, among other things, heart rate and carbon monoxide and oxygen saturation levels. The physiologic sensors are connected to a transmitting apparatus attached to the SCBA. Each SCBA transmitter sends output data from the physiologic sensors, along with the wearer's location information, to a remote base unit. A processor within the base unit compiles the physiologic and location data. In this way, the base unit monitors the particular physiologic status of an individual in a hazardous environment from a remote location. A further embodiment of the present invention includes monitoring the physiologic status and location of groups of individuals by combining a plurality of base units into a station unit.

12 Claims, 16 Drawing Sheets

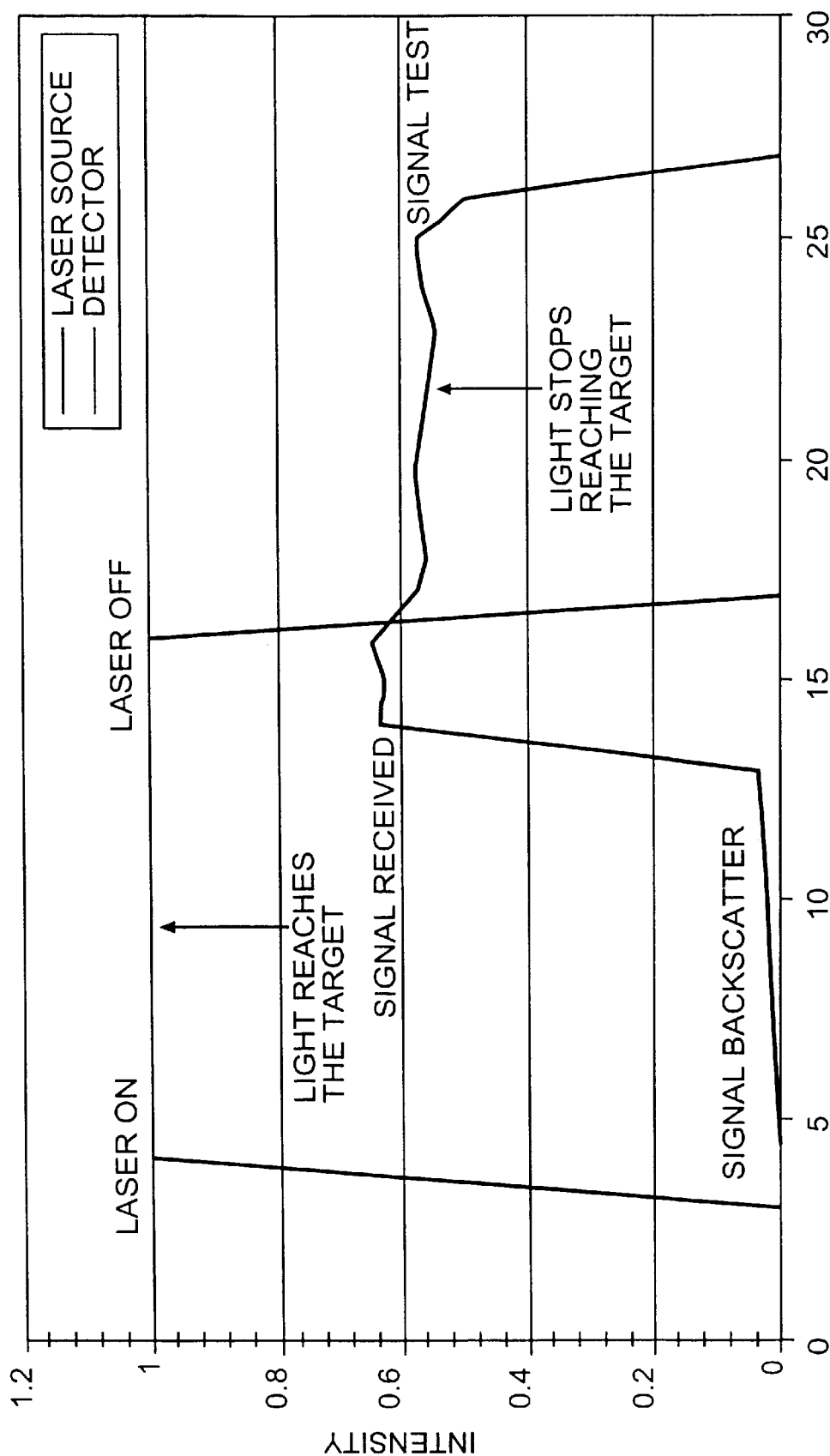

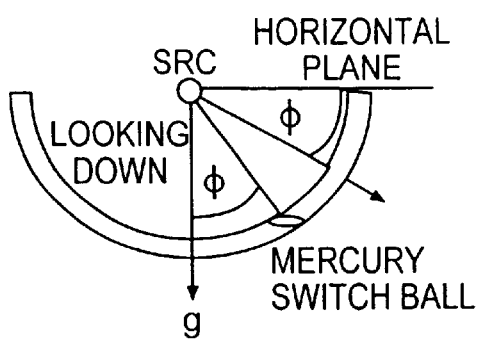
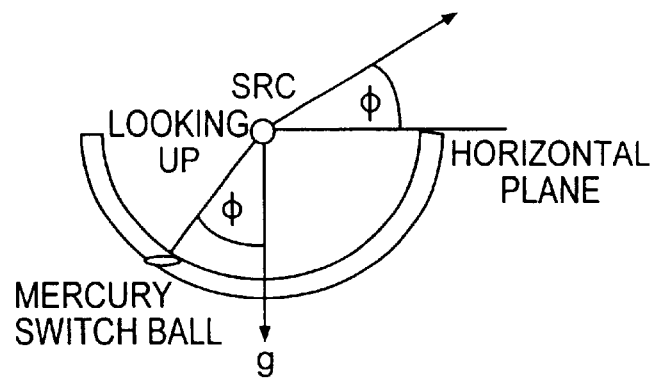
FIG. 8  FIG. 9
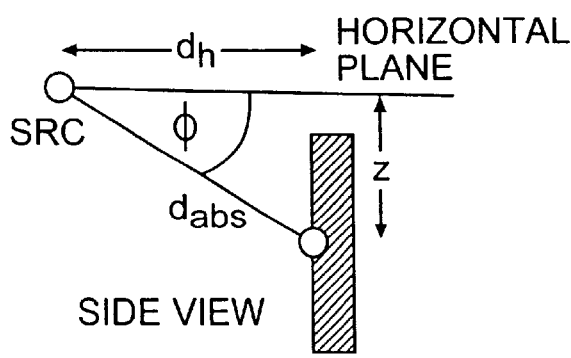
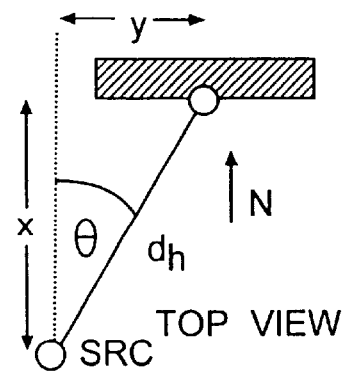
FIG. 10  FIG. 11

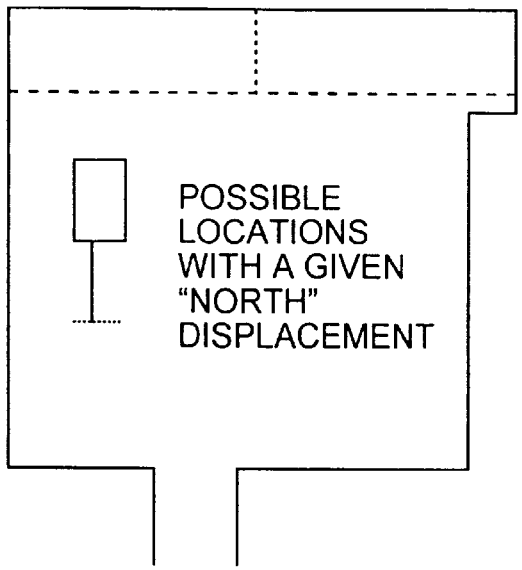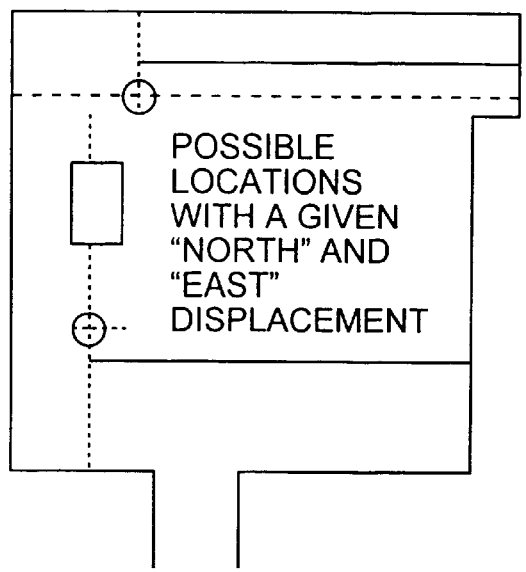
FIG. 21  FIG. 22
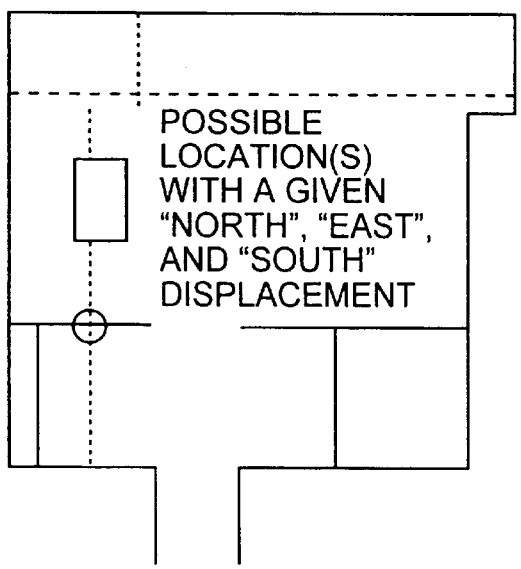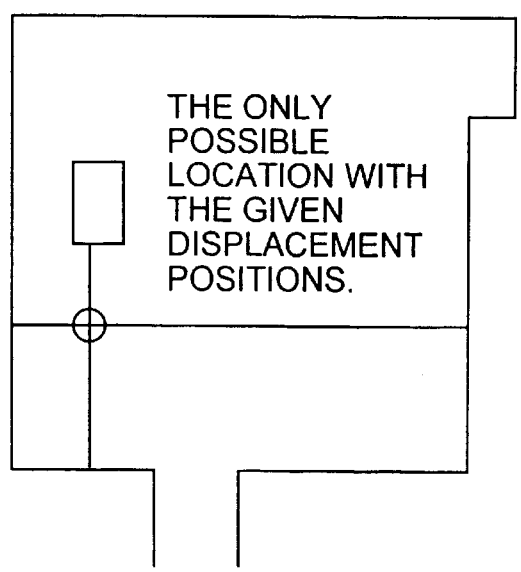
FIG. 23  FIG. 24

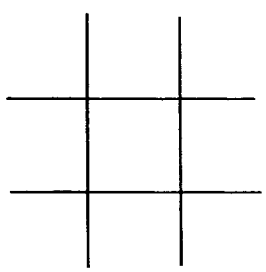
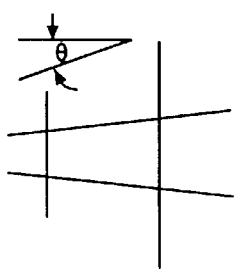
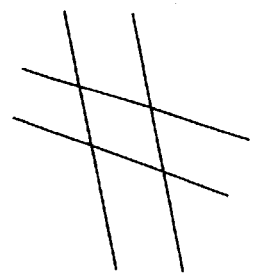
FIG. 25  FIG. 26  FIG. 27
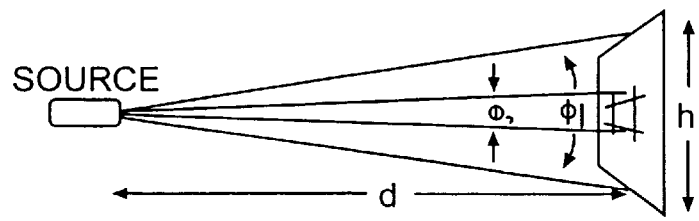
FIG. 28
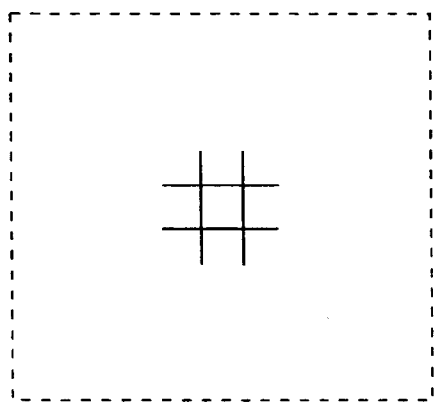
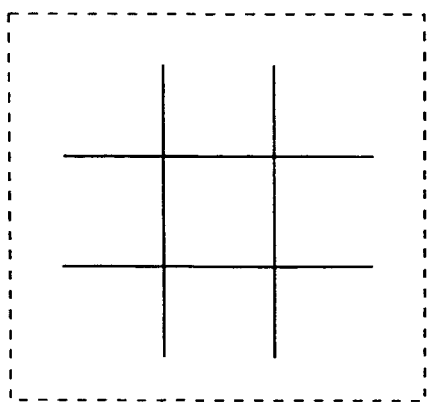
FIG. 29  FIG. 30

INTEGRATED PHYSIOLOGIC SENSOR SYSTEM

CROSS-REFERENCE TO RELATED APPLICATION

This is a division of application Ser. No. 09/134,483, filed Aug. 14, 1998, now issued as U.S. Pat. No. 6,199,550.

FIELD OF THE INVENTION

This invention relates to the field of monitoring systems. More particularly, this invention relates to the sensor system self-contained breathing apparatus (SCBA) used by personnel in hazardous conditions.

BACKGROUND OF THE INVENTION

Many occupations require personnel to operate under extreme physical stress and/or hazardous conditions. Such occupations are, for example, firefighters, mine workers, military personnel, ship yard workers, chemical industry personnel, athletes, permit required confined space applications (as defined by OSHA) or personnel working in asbestos removal projects. The physiologic condition of personnel working in hazardous environments, and/or with high physical stress is a vital concern. It is desirable that the physiologic condition can be monitored on an ongoing real time basis. In particular, it is desirable to monitor the physiologic condition of the personnel in combination with the physical location of the personnel.

Generally, physiologic sensor systems have been developed to monitor patient's physiologic status in a clinical setting. Monitoring healthy personnel working under stressful or hazardous conditions, however, differs in several essential ways from monitoring patients in a clinical setting. While some physiological parameters will likely be common in both instances, the types of sensors used and the data processing and data management is different in critical ways. Most non-invasive patient monitoring focuses on detection of alterations in temperature, heart rate or rhythm, blood pressure or oxygen saturation. These observations are recorded and analyzed under environmentally controlled conditions with the patient at rest or engaged in tightly limited physical activities. Under these controlled conditions, it is a relatively simple matter to attribute deviations from baseline values to pathologic states that require medical attention. Additionally, real time recognition of potentially significant physiologic events in monitored patients does not require complex analysis. Relatively narrow limits defining tolerable values can be established and readings outside of these limits can then be used to trigger alarms. The medical personnel monitoring the output of the sensor instrumentation would then perform the more complex information processing including integration of the data from the sensor array with the clinical history and circumstances of the patient.

Application of current real time medical monitoring technology to personnel engaged in stressful activities such as, fire suppression, chemical clean up, asbestos removal or military activities, presents substantially different circumstances. Specifically, access to the biological,data of the worker must be gained without compromising response times or compromising the protective equipment worn by the personnel. This means that sensors have to be incorporated into the equipment such that the signals from the sensors can be reliably transduced and amplified without motion artifact regardless of the local sweating, incident trauma or other stress on the personnel. This must be accomplished while maintaining both the integrity of the protective material and the sensor seals.

For example, a firefighter cannot be further encumbered by either significant weight or by extensive wiring or tethering. The sensors and supporting instrumentation need to be able to withstand environmental conditions ranging from subzero to blast furnace temperatures, toxic atmospheres and the inevitable physical battering. Beyond the physical restraints placed on the sensor system, the sensor system must also be able to react to extreme variability in vital parameter values that characterize individual physiologic response to extreme environmental stress and exertion. Furthermore, the sensor system must be able to provide useful real-time information for decision makers receiving the processed output from the sensors.

Specifically, in a firefighting environment, fire ground is a high hazard environment that requires constant vigilance by emergency responders. Personnel working in a fire scene must be able to quickly identify and adapt to rapidly evolving threats. Any information from a physiologic or environmental monitoring system must be presented to such individual firefighters in a clearly useful format while minimizing non-essential distractions. A continuous numeric readout of oxygen saturation values, for instance, would divert a firefighter's attention from his surroundings and divert his attention away from more urgent fire ground queues. The information from an individual firefighter's entire sensor array must be returned to him in a format that simply indicates the ability of it's safe to continue or it's necessary to evacuate the hazard zone. While it is important that only this minimal critical level of data be presented to the firefighter, the amount of information necessary to return this minimal level of data must be monitored on a continuing basis and analyzed over a significant period of time. Particularly, more specific information concerning physiologic parameters such as pulse rate, oxygen saturation, or carbon monoxide, must be available to personnel keeping track of larger numbers of workers in the hazardous situation.

The prior art discloses apparatus that is directed to individual sensor problems but does not disclose apparatus that integrates a sensor system directed at critical physiologic parameters with a position sensor system and apparatus for real time processing and display of the sensor data. For example, the prior art discloses general sensors mounted in a self-contained breathing apparatus mask. This art does not disclose specific sensors for sensing critical parameters monitored in hazardous environments. It also does not disclose any solution to the problem of processing the sensor information in real time. Other references disclose monitoring systems for physiologic parameters that are not integrated into SCBA systems and that do not display different information to various personnel.

OBJECTS OF THE INVENTION

It is an object of this invention to monitor the physiologic status of personnel in stressful and hazardous environments.

It is still a further object of the present invention to monitor the location of personnel in hazardous environments.

It is a further object of the present invention to indicate to an individual in a hazardous situation a current physiologic status.

It is still a further object of this present invention to monitor the physiologic status and location of a variety of individuals operating in a hazardous environment.

It is yet a further object of the present invention to guide an individual out of a hazardous situation.

SUMMARY OF THE INVENTION

An embodiment of the present invention comprises a self-contained breathing apparatus (SCBA) mask that incorporates a series of physiologic sensors. These physiologic sensors are mounted on the interior of the SCBA mask in such a way as to contact the facial skin of an individual wearing the mask. The physiologic sensors monitor, among other things, heart rate and carbon monoxide and oxygen saturation levels. The physiologic sensors are connected to a transmitting apparatus attached to the SCBA. The SCBA transmitter sends output data from the physiologic sensors to a remote processor. The SCBA transmitter also sends location information of the individual wearing the SCBA mask to the remote processor. The remote processor compiles the physiologic and location data for the wearer of the SCBA and transmits a signal back to the SCBA receiver which, in turn, sends a signal to a display integrated into a SCBA mask. The display indicates to the individual his physiologic status. The display incorporates indicator lights are integrated into the mask of the SCBA to indicate, for example, when bottled air must be switched on, to indicate the emergency situation of the wearer and/or to indicate the direction that the wearer of the SCBA is going. The processor associated with the transmitter also monitors groups of individuals wearing the SCBA masks. In this way, the particular status of several individuals in the hazardous environment can be monitored at once and their situation known over a period of time in the hazardous conditions. Specifically, the physiologic condition of the group can be monitored to track the changes in the group condition over the time that the group is exposed to the hazardous environment.

DESCRIPTION OF THE DRAWING

FIG. 7 is representation of measurement data that may be operated on by the measurement system according to one embodiment of the present invention.

FIG. 8 is a representation of the quantities to be measured according to one embodiment of the prevent invention.

FIG. 9 is a representation of the quantities to be measured according to one embodiment of the prevent invention.

FIG. 10 representation of the quantities to be measured according to one embodiment of the prevent invention.

FIG. 11 representation of the quantities to be measured according to one embodiment of the prevent invention.

FIG. 21 is a representation of a partial map created from measurement data collected from a measurement system according to one embodiment of the present invention.

FIG. 22 is a representation of a partial map created from measurement data collected from a measurement system according to one embodiment of the present invention.

FIG. 23 is a representation of a partial map created from measurement data collected from a measurement system according to one embodiment of the present invention.

FIG. 24 is a representation of a partial map created from measurement data collected from a measurement system according to one embodiment of the present invention.

FIG. 25 is a representation of a measurement grid according to one embodiment of the present invention.

FIG. 26 is a representation of a measurement grid according to one embodiment of the present invention.

FIG. 27 is a representation of a measurement grid according to one embodiment of the present invention.

FIG. 28 is a representation of a measurement system according to one embodiment of the present invention.

FIG. 29 is a representation of a measurement grid according to one embodiment of the present invention.

FIG. 30 is a representation of a measurement grid according to one embodiment of the present invention.

DESCRIPTION OF THE PREFERRED EMBODIMENT

Figure 1:
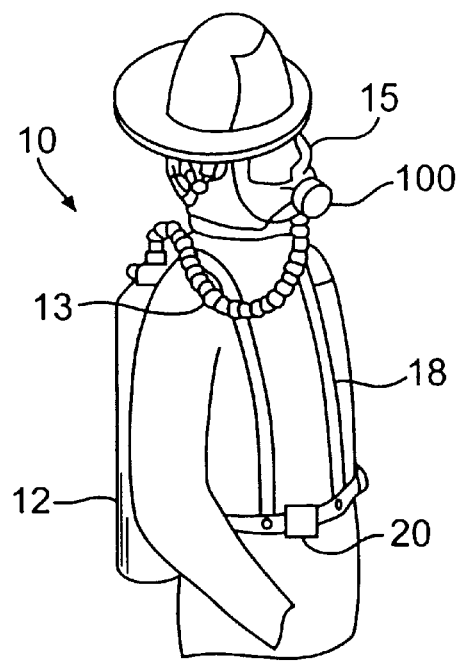
FIG. 1 illustrates a self-contained breathing apparatus according to one embodiment of the present invention as it is used by an individual.
Figure 2:
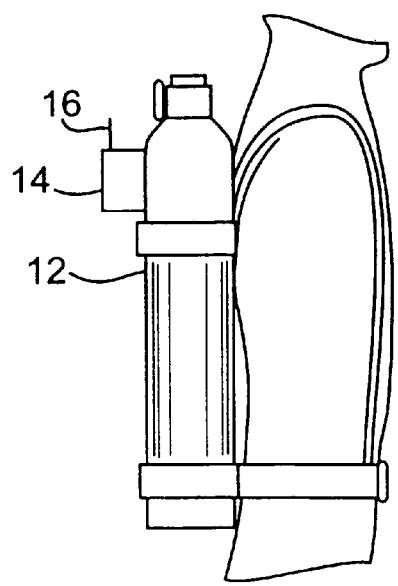
FIG. 2 illustrates a side view of a self-contained breathing apparatus according to one embodiment of the present invention as it is used by an individual.

FIG. 1 generally illustrates a Self-Contained Breathing Apparatus (SCBA) as typically used by individuals. The SCBA 10 has a mask body portion 100 that snugly fits to the face of an individual. The SCBA 10 also incorporates a clear shield portion 15 through which the individual sees. The SCBA also incorporates a source of bottled air 12 connected to the mask portion through a breathing tube 13. The equipment includes a harness 18 which holds the air tank at the workers back and a personal alert safety system 20 that is held on the worker by, for example, mounting it on the harness. The PASS senses an emergency situation such as lack of worker motion for a period of time. The PASS activates an alarm if the worker remains motionless for a predetermined period. It is common that after twenty seconds of detecting no motion, the PASS sounds a chirp to remind the worker that it will activate the full alarm in ten seconds if the worker remains motionless, so the worker can move to avoid a false alarm. The alarm usually includes a device that produces a loud sound. As illustrated in FIG. 2, the SCBA also includes a radio transmitter 14 that transmits through antenna 16 an emergency signal to a command station that may be on a nearby fire truck to alert others that a fireman is in danger.

Figure 3:
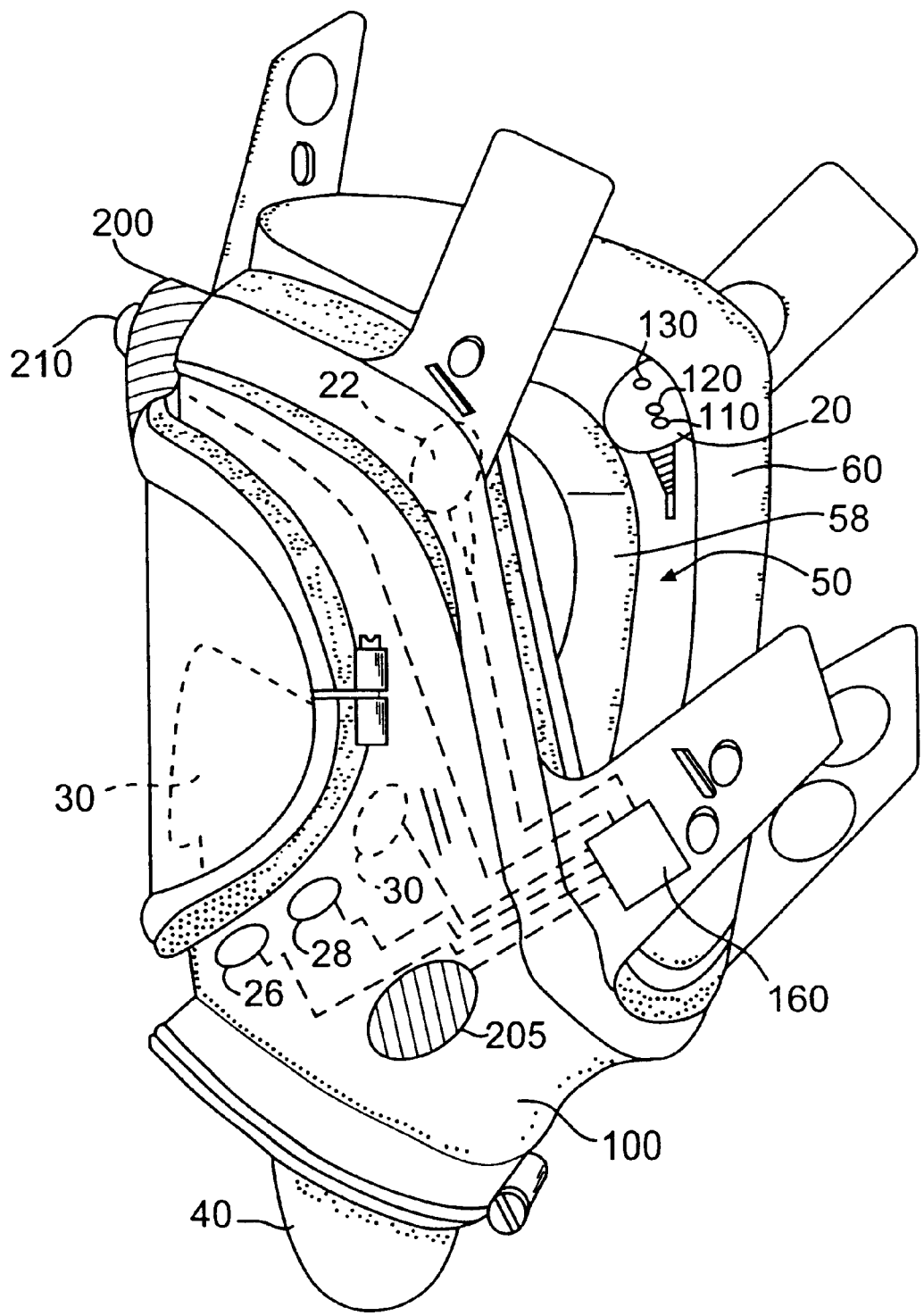
FIG. 3 illustrates a mask body of a self-contained breathing apparatus according to one embodiment of the present invention.

FIG. 3 illustrates the mask body 100 of the SCBA in the present invention. The mask body includes a viewing window 20 and an inner half-mask 30 which, in turn, includes an exhale valve 40. The mask body 100 is surrounded about the periphery by a sealing rim 50 which accommodates sensors 20, 22 in the forehead region of the wearer of the mask. The sealing rim 50 of the mask can include two mutually adjacent sealing beads 60 and 58 which extend around the peripheral region of the mask. The mutually adjacent sealing beads conjointly define a cavity therebetween and the sensor 6 is seated in the cavity so as to be in contact engagement with the wearer of the mask when the mask is worn. An additional contact thermometer 70 can be mounted on the side of the sealing rim 50 opposite sensor 20 in order to detect the body temperature.

Sensor 20 monitors carbon monoxide and sensor 22 monitors heart rate and oxygen saturation levels in an individual's bloodstream. The mask also incorporates sensors 26, 28 and 30. Sensor 26 monitors external temperature, sensor 28 monitors cyanides or other potential constituents of smoke and sensor 30 monitors exhaled carbon dioxide. Sensor 30 is conveniently constructed to be in the respiratory path of the SCBA. The sensors 20 and 22 shown as in FIG. 3 are illustrated in more detail in FIG. 4.

The oxygen saturation sensor 22 measures the percentage of blood cells that are occupied with oxygen ($S_pO_2$) versus empty. Sensor 22 is capable of distinguishing between blood cells occupied by oxygen and blood cells occupied by carbon monoxide. Carbon monoxide makes a stronger bond to blood cells than oxygen does, and thus, prevents the exchange of oxygen and carbon dioxide causing hypoxia in the person. A carbon monoxide sensor 20 can be used to determine the concentration of carboxy-hemoglobin ($COH_b$) in the body. True oxygen saturation can be determine by subtracting $COH_b$ from $S_pO_2$. A carbon dioxide $CO_2$ sensor is placed in the exhaled respiratory path of the SCBA. This device measures End-Tidal $CO_2$ ($EtCO_2$), or the amount (partial pressure) of $CO_2$ in exhaled breath. If the amount of $EtCO_2$ drops significantly below 5% (or about 35 mmHg), the person wearing the mask is not achieving good oxygen-carbon dioxide exchange.

Figure 4:
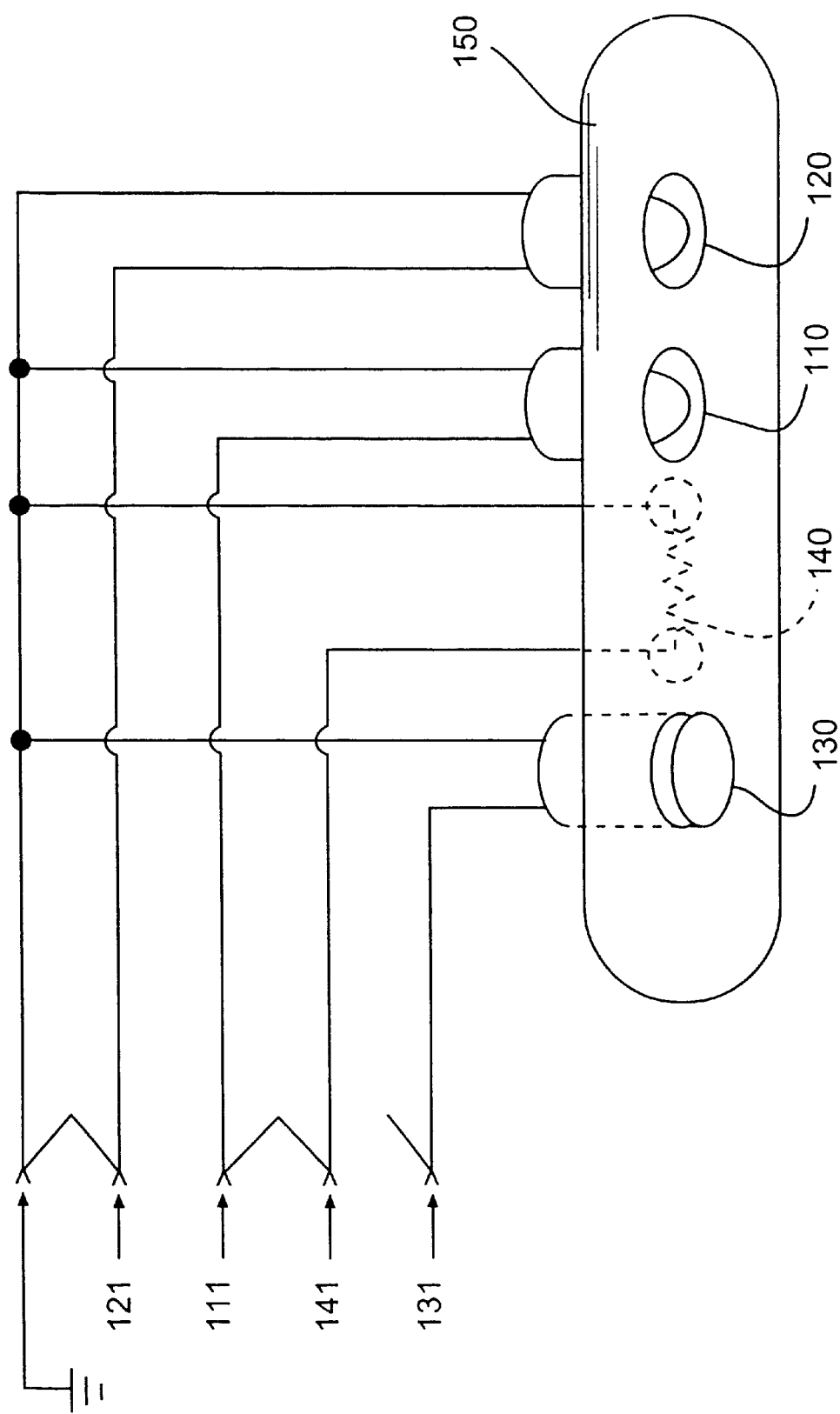
FIG. 4 is a diagramtic illustration of a pulse oximeter sensor for use in a self-contained breathing apparatus according to one embodiment of the present invention.

FIG. 4 illustrates a pulse oximeter of the type wherein light of two different wavelengths is passed through any pulsatile tissue bed, such as a side of a face or the scalp, so as to be modulated by the pulsatile component of arterial blood therein, and thereby allowing an indication of oxygen saturation, blood perfusion and heart rate. The level of incident light is continually adjusted for optimal detection of the pulsatile component, while permitting accommodation to variable attenuations due to skin color, flesh thickness and other invariants. At significant slope reversal of.the pulsatile component to negative (indicating a wave maximum), wave form analysis of blood flow occurs.

A quotient of the pulsatile component of light transmission is measured for each of two wavelengths by direct digital tracking. The respective quotients are thereafter converted to a ratio, which ratio may be thereafter fitted to a curve of independently derived of oxygen saturation for the purpose of calibration. The saturation versus ratio calibration curve may be characterized by various mathematical techniques including polynomial expansion whereby the coefficients of the polynomial specify the curve. An output of pulse rate, pulsatile flow and oxygen saturation is given. An incident light source duty cycle is chosen to be at least 1 in 4 so that noise, inevitably present in the signal, may be substantially eliminated and filtered.

In FIG. 4, a part-schematic, part-perspective view of the optical sensor is shown. A flexible base material 150 is provided. Incorporated into base material 150 at suitably spaced intervals are the electrical components of sensor. Photoelectric sensor 130 is attached to the outside of base 150 and protrudes slightly from the underside of base 150. Sensor 130 has ground wire G and lead wire 131. Light emitting diode 110, typically emitting frequencies in the infrared range of the spectrum, is mounted to and pierces base 150 in a similar manner to sensor 130 and at a distance from sensor 130 of approximately several centimeters or less. LED 110 is connected to ground wire G and has input lead wire 111. Placed in proximity to LED 110 is a second LED 120, typically having wavelength emission characteristics in the red range of the spectrum. LED 120 attaches to ground wire G and has input lead wire 121. Resistor 140 is shown mounted to base 150 between sensor 130 and LED 110. However, the physical location of resistor 140 is not important and it may be mounted to sensor at any other convenient location. Resistor 140 has input lead wire 141 and is connected to ground wire G. Wires G, 111, 121, 131, 141 lead to connector 152 so that sensor may be readily disconnected from the processor electronics 160. In an alternative embodiment, the LEDs may not be wired together or may be contained in separate base components.

The sensor of FIG. 4 is constructed in the following manner: LEDs 110, 120 are selected from batches of LEDs with generally known wavelength characteristics. The exact wavelength characteristics of the specific LEDs 110, 120 chosen are determined at this time through readily available metering means. Resistor 140 or a similar impedance reference is then selected to have an impedance or specifically a resistance whose amount is exactly specified by a table made available to the factor technician for this purpose, of all possible wavelength combinations which may be expected to be encountered from the available supplies of LEDs. The following table is-an example of how a single resistor 140 might be selected for any hypothetical combination of LED's 110, 120 in a case where each has only two possible wavelengths:

TABLE A

| Resistor 40 | LED 10 | LED 20 |
|---|---|---|
| 150 ohms | 940 nM | 660 nM |
| 160 ohms | 950 nM | 660 nM |

TABLE A-continued

| Resistor 40 | LED 10 | LED 20 |
|---|---|---|
| 170 ohms | 940 nM | 670 nM |
| 180 ohms | 950 nM | 670 nM |

A typical sensor will have an infrared LED 110 of wavelength 940 nanometers and a red LED 120 of wavelength 660 nanometers. According to the above table, a sensor having such wavelength characteristics will be supplied at the factory with a resistor 140 of one, and only one, resistance value, in this case shown to be 150 ohms.

Figure 5:
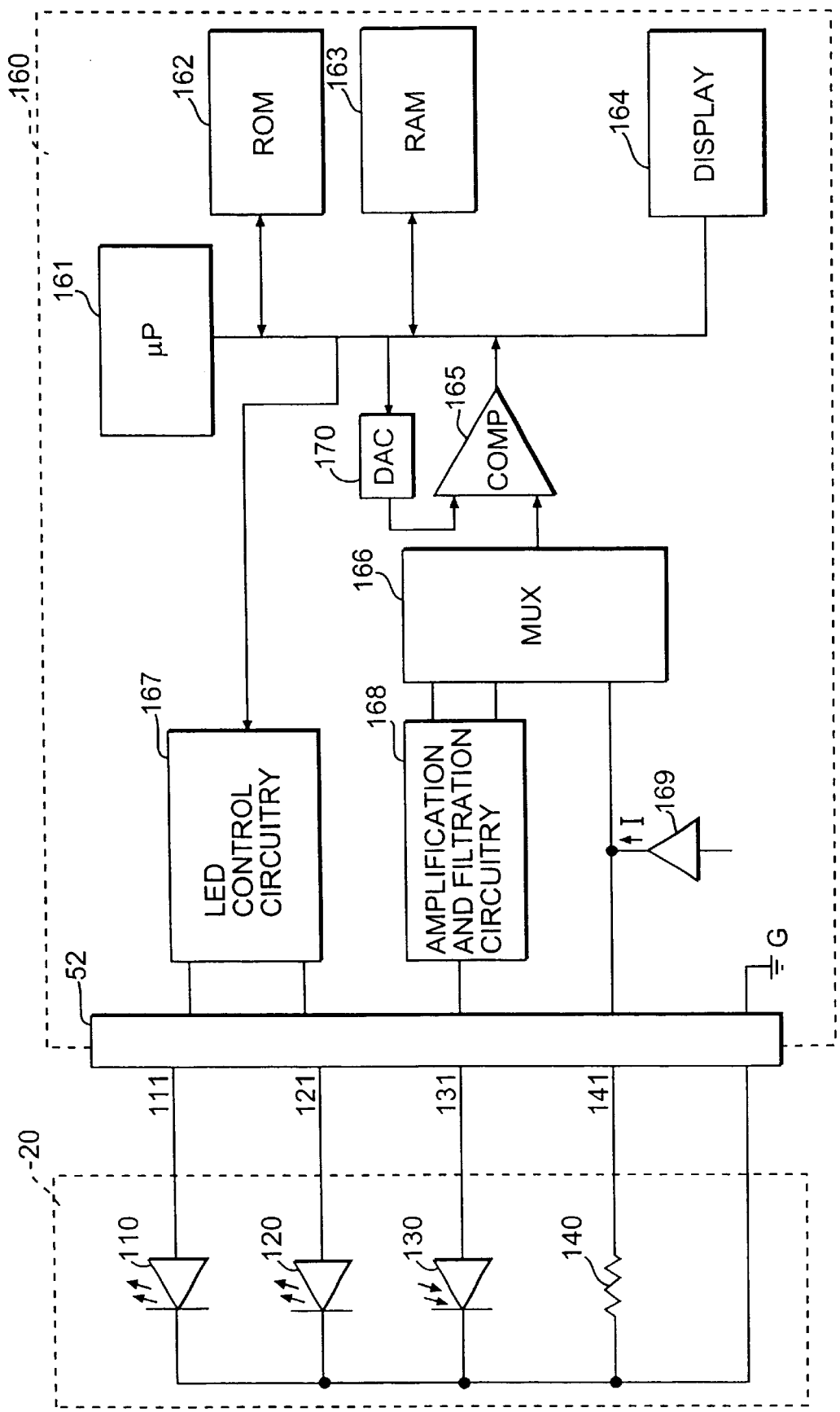
FIG. 5 is a block diagram of a processor used in conjunction with a pulse oximeter in a self-contained breathing apparatus according to one embodiment of the present invention.

The sensor illustrated in FIG. 4 is designed for use in connection with a processor 160 illustrated in FIG. 5 and designed to operate in conjunction with two LEDs 110, 120 sequentially transmitting light to a single sensor 130. However, the mechanism of the instant invention works equally well for processors requiring only a single LED and single or multiple photo sensors. The processor contains a microprocessor 161, and a read only memory 162 and random access memory 163. Table A (the same table used for calibrating sensor at the factory) no matter how extensive, may be easily programmed into ROM 162 at the time processor is fabricated. Current I from current source 169 is passed through resistor 140. The resulting voltage (per Ohm's law) is passed through multiplexor 166 through comparator 165, to microprocessor 161.

Microprocessor 161 may be programmed to calculate the resistance of resistor 140 and thereafter to look up the wavelengths of LEDs 110, 120 from Table A in ROM 162. Microprocessor 161 is also programmed to itself recalibrate the optical comparison circuitry of oximeter 160 once the wavelengths of LEDs 110, 120 are known. By this means, it is not required to recalibrate by hand oximeter 160 for each new sensor nor, alternatively, to require that LED's 110, 120 be of precisely standardized wavelengths.

Basically, for each heart beat, fresh arterial blood is pumped into the capillaries of the person wearing the SCBA mask, thereby causing a periodic increase and decrease in light intensity observed by sensor 130. The oxygen saturation of hemoglobin in the pulsatile blood may be determined by the processor 160. For any known wavelength, there is a known extinction coefficient B. Given B and measuring the intensity of the diffused light received by sensor 130 the oxygen saturation can be computed and displayed. In fact, the coefficients B of the various wavelengths of table A can be substituted for the wavelengths directly when the table is programmed into ROM 162, thereby eliminating a computation step.

Microprocessor 161, through LED control circuitry 167, operates LEDs 110, 120. Light from LEDs 110, 120 results in current in detector 130 which passes through amplification and filtration circuitry 168 to multiplexor 166. Comparator 165 and a digital to analog converter 170 are operative as an analog to digital converter means to present a digital signal to the microprocessor 161, thereby allowing microprocessor 161 to determine oxygen saturation and/or pulse rate. Results are shown on display 164.

In addition to the sensors 20, 22, 26, 28 and 30, the SCBA mask illustrated in FIG. 3 incorporates multiple position sensor systems 200 and 205 respectively. The position sensor system incorporates a distance measurement system in which a source of electromagnetic radiation 210 emits, for example, a laser beam and detects the reflected light from that beam. As an alternative embodiment the multiple sensor systems could be mounted on an air bottle harness, helmet or other piece of gear. The only requirement is that each set of sensors has its own known orientation with respect to any other set of sensors.

Figure 6:
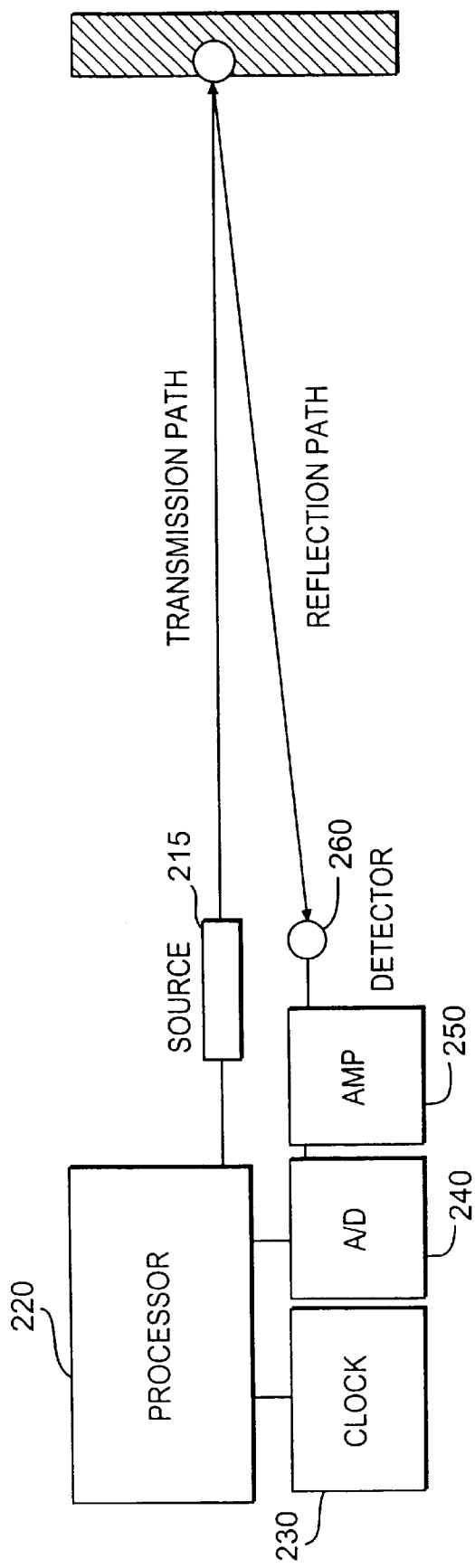
FIG. 6 is a schematic illustration of a distance measuring system for use in-a position locating system in a self-contained breathing apparatus according to one embodiment of the present invention.

FIG. 6 is a schematic illustration of the structure of the distance measurement system and its operation. For example, a laser source 215 is activated by the electronics system including a processor 220, clock 230, analog to digital (A/D) circuitry 240 and sensor amplifier 250. The beam of light travels through the air (medium) until it reaches an object (for example a wall). The light is reflected by the target object back towards the laser source (as well as any other line-of-site direction) with greatly reduced intensity. A light detector 260 (photodiode, photomultiplier tube, etc.), set to search for the same frequency of light as the source then begins to detect the reflected light. The time difference between the emission of light and its detection is carefully measured. The accuracy of the system will be proportional to the accuracy of the time measurement. The time measured represents the time taken by light to travel from the source to the target and from the target to the detector. This distance is twice the distance between the source and the target. Using the speed of light multiplied by the time measured and divided in half will provide the distance (Equation 1). For the example in FIG. 7, the time between transmission and detection is 10 nanoseconds (10× $10^9$ sec.). Thus the distance between the source and target is 5 nanoseconds multiplied by the speed of light ($2.99792458 \times 10^8$ meters/second) for an answer of 1.499 meters. Thus each nanosecond is approximately 0.29979 meters of distance.

Equation 1:

$$dist = \frac{(\text{speed\_of\_light}) * (time_{detection} - time_{transmission})}{2}$$

The entire process can be repeated by shutting the laser off and measuring the time before the detector can no longer see the signal. Repeating this process rapidly (pulsing) allows several measurements to be taken in a short period of time. The results of this measurement can be averaged (and the worst data sets discarded) to improve the accuracy of any readings reported to the user or the system.

The electronics will also cause a small discrepancy in the measurements, as the signals must travel through the wires and circuits. These signals also travels at the speed of light, thus if the signal must travel through 30 centimeters of wire to go from the processor to the source and detector, an extra two nanoseconds will always be added to measured times. This is a constant offset regardless of the distance to the target, and can thus be accounted for with a calibration factor (Equation 2).

Equation 2:

$$dist = \frac{(\text{speed\_of\_light}) * (time_{detection} - time_{transmission} - time_{calibration})}{2}$$

Alternatively, a method of measuring both the time and the phase of the reflected light wave can also be used to achieve higher levels of accuracy without the use of high frequency clocks. In this method, the accuracy will be highly dependent upon the frequency, $f$, (or alternatively the wavelength, $\lambda$) of the light source (Equation 3). For example a wave traveling at 633 nanometers will be detected with a phase component, each 1 degree of phase would correlate to a distance of 1.76 nanometers. Once again, allowing for both the transmission and reflection paths, the total accuracy of a system discriminating one degree of phase would be 0.88 nanometers.

$$\lambda = v_{light}/f \quad \text{Equation 3:}$$

Furthermore, by using multiple wavelengths of light and comparing the phase differences between them, a very accurate measurement system can be developed. This type of a system would allow very precise measurements without a high-speed clock. The pattern of phase measurement will only begin to repeat itself after it has traveled through the product of each of the wavelengths (Equation 4). In this case, the timing circuitry needs to be accurate enough to select which distance_repetition_cycle (Equation 5), and then add that to the fine distance calculations performed by phase discrimination (Equation 6).

$$\text{distance\_to\_repetition} = \lambda_1 \times \lambda_2 \ldots \times \lambda_n \quad \text{Equation 4:}$$

Equation 5:
$$\text{time\_accuracy} = \frac{\text{dist\_repetition}}{\text{speed\_of\_light}}$$

For example, if three light waves were selected with frequencies of $\lambda_1$=633 nm, $\lambda_2$=580 nm, and $\lambda_3$=532 nm, the phase pattern would repeat once every 0.19531848 meters. In this case, according to Table 1, we would only require a sampling frequency on the order of 2 GHz (actually about 1.33 GHz). If our clock indicated that 16 time cycles had elapsed (~0.195 meters/cycle) and that our phase measurements were $\theta_1$=0.456 radians (26.13°), $\theta_2$=1.65 radians (94.54°), and $\theta_3$=5.112 radians (292.9°), then the $\text{dist}_{phase}$= (45.94×152.31×432.84)/195318480=0.0155 nm. Thus, the total measured distance would be 1562547840.008 nm or 1.562547840008 meters.

Equation 6:
$$\text{dist}_{phase} = \frac{\frac{\theta_1]_0^{2\pi} \times \lambda_1}{2\pi} \times \frac{\theta_2]_0^{2\pi} \times \lambda_2}{2\pi} \times \ldots \times \frac{\theta_n]_0^{2\pi} \times \lambda_n}{2\pi}}{\text{dist\_repetition}}$$

In addition to the distance measurement system, the position sensor system 200 incorporates a direction sensor system. The direction sensor system further incorporates a magnometer system which measures the yaw (angle relative to a fixed direction such as magnetic north) of the electromagnetic source relative to a fixed direction. The direction sensor system also incorporates a mercury switch (FIG. 8 & FIG. 9) (or similar device) is used to measure the pitch (angle of electromagnetic radiation source relative to a horizontal plane). When the source decreases its pitch, as in looking down, gravity causes a mercury ball to slide forward. As the source increases in pitch, the mercury ball slides back (following the vector for gravity, g). The switch itself in a potentiometer (variable resistor) whose resistance ranges from 0 ohms to some value of ohms (typically 10 kohms) as the switch slides from −90 degrees (looking straight down) to +90 degree (looking straight up). A current is passed across the potentiometer, creating a voltage which can be measured by an analog to digital conversion circuit. The range finding system provides us with the value for $d_{abs}$, $\phi$ is the pitch (inclination or declination) angle and $\theta$ is the displacement from a fixed vector (yaw or skew). In this case the fixed direction is magnetic north (FIG. 10 & FIG. 11). The vertical displacement of the target from the source is given by:

$$z = d_{abs} \times \sin\theta \quad \text{Equation 13:}$$

The total horizontal displacement, $d_h$, (distance "up") is then given by:

$$d_h = d_{abs} \times \cos\theta \quad \text{Equation 14:}$$

The x-axis displacement (distance "north") is then given by:

$$x = d_h \times \cos\theta \quad \text{Equation 15:}$$

And the y axis displacement (distance "east") is given by:

$$y = d_h \times \sin\theta \quad \text{Equation 16:}$$

Figure 12:
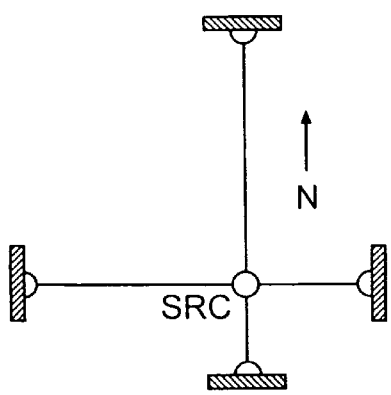
FIG. 12 representation of the quantities to be measured according to one embodiment of the prevent invention.
Figure 13:
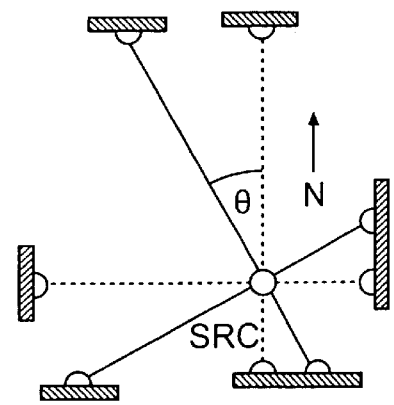
FIG. 13 representation of the quantities to be measured according to one embodiment of the prevent invention.
Figure 14:
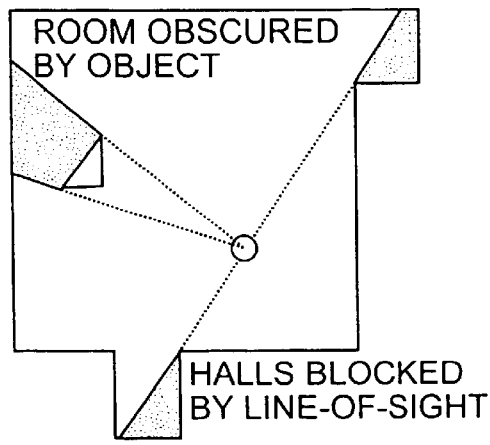
FIG. 14 is a representation of a room to be measured according to one embodiment of the present invention.

By placing multiple systems for the acquisition of distance to target, at fixed orientations (pitch and yaw angles) a complete picture or map can be developed. The following example illustrates this concept in two dimensions (horizontal plane, no pitch). The source has been equipped with four distance measuring systems, each oriented at 90° angle from the others. If the target were facing north (yaw, $\theta$=0°) then distances to the north, south, east, and west would all be measured (FIG. 12). As the source turns through an angle $\theta$, new target positions area calculated (FIG. 13). Eventually this process creates a complete map of the entire area Visible to the source through line of sight (FIG. 14). The system will initially have no concept of the location and orientation of the walls of the structures. It will only be able to generate a "dot-to-dot" type map (FIG. 15) where the angle and distances to the source are known to be clear of interference (a map of the clear spaces rather than a map of the structure. Software algorithms are then used to connect these dots using a set of rules:

1. The pathway between the source and the target must be clear (by definition).
2. No deductions should be made about areas blocked by line of site until the source has moved enough to fill in the missing information.
3. The target positions (dots) can then be connected to the nearest adjoining positions, so long as the connection does not cross any obscured areas.

Figure 15:
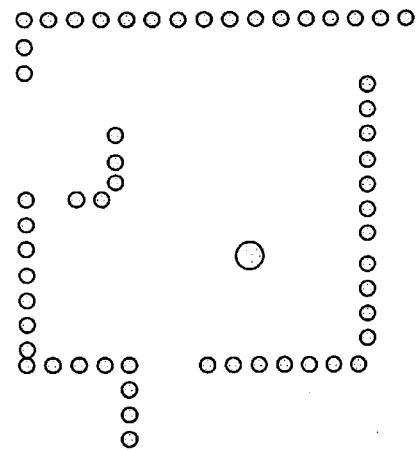
FIG. 15 is a representation of the resulting measurement data collected in measuring a room according to one embodiment of the present invention.
Figure 16:
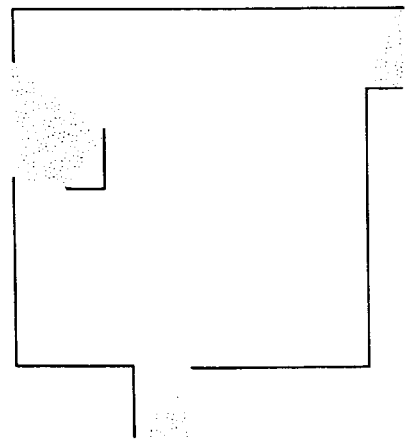
FIG. 16 is a representation of a partial map created from measurement data collected from a measurement system according to one embodiment of the present invention.

Using this method, the targets (dots) in FIG. 15 create a partial map of the room (as known from the initial source position) as shown in FIG. 16.

Figure 17:
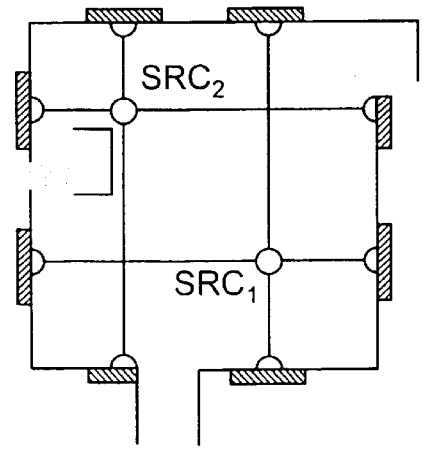
FIG. 17 is a representation of a partial map created from measurement data collected from a measurement system according to one embodiment of the present invention.

In FIG. 14, there is no way to distinguish if the "hallways" blocked by the line of sight are actually halls, closets, or alcoves. As the source moves throughout the structure, new positions and angles of clear spaces are generated. This process eventually fills in the information missing due to line of sight limitations from any one position (FIG. 17) by using either multiple positions of the same source or simultaneous multiple sources. It must be understood that while these examples use and create a two-dimensional map, the entire process can be extended into a third dimension for a measurement of height.

For proper operation, the position of the source must be known as the source moves from place to place. The above mentioned equations will create a map of the target relative to the current position of the source; however, it (at least initially) does not calculate the position of the source in any absolute sense. In general, this system works by calculating the movement of the source from data provided by accelerometers. The accelerometers are mounted to provide data for each of the ordinal vectors x ("north"), y ("east"), and z ("up"). In general, the equations for motion are:

$$v_{x1} = v_{x10} + a_{x1}x(t_1 - t_0) \qquad \text{Equation 17:}$$

Figure 18:
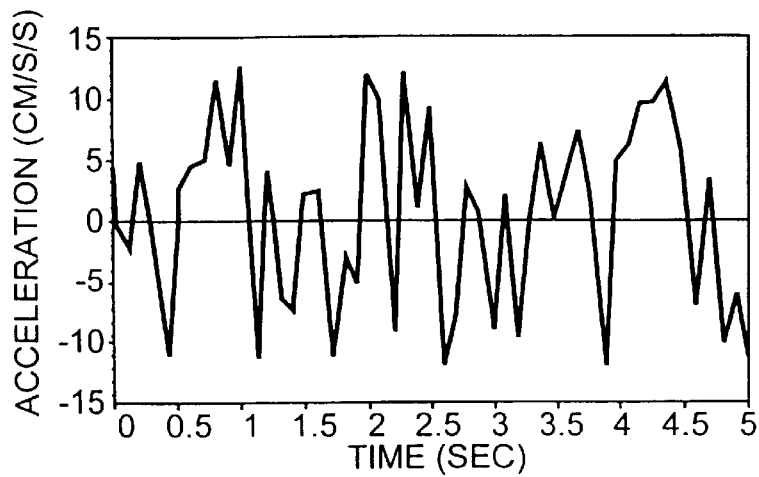
FIG. 18 is a representation of the resulting measurement data collected in measuring a room according to one embodiment of the present invention.
Figure 19:
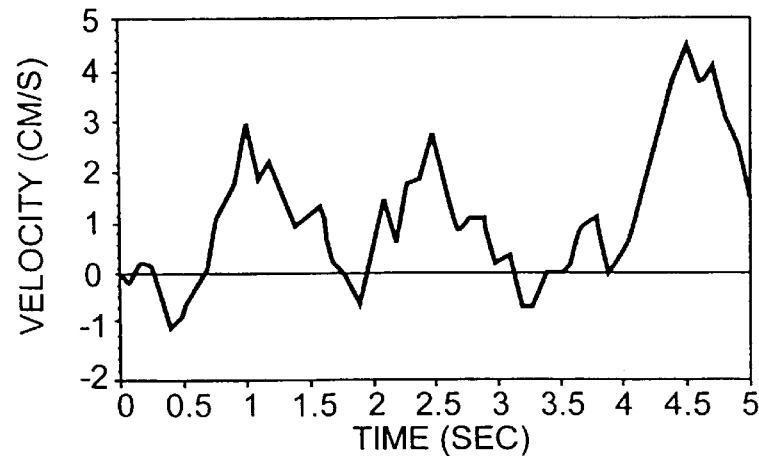
FIG. 19 is a representation of the resulting measurement data collected in measuring a room according to one embodiment of the present invention.

The current velocity of the source (FIG. 19) is equal to the measured acceleration (FIG. 18) multiplied by the increment of time added to the old velocity. Likewise the cumulative displacement of the source can be calculated as:

$$x_1 = x_0 + v_{x1}x(t_1 - t_0) \qquad \text{Equation 18:}$$

Figure 20:
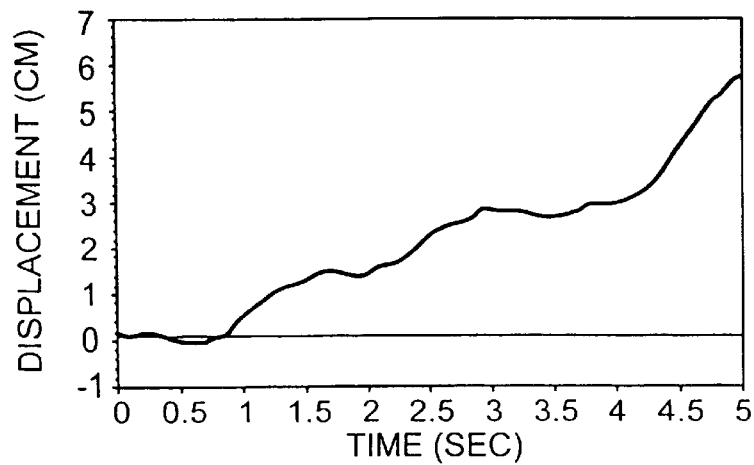
FIG. 20 is a representation of the resulting measurement data collected in measuring a room according to one embodiment of the present invention.

The new displacement (FIG. 20) is equal to the calculated velocity multiplied by the increment of time added to the old displacement.

Once data creating the map of the structure has been gathered, the position of the source can be determined not only by measuring the dead reckoning displacement, but by using the position information. The following examples have been simplified such that all the angles are either θ=0° ("north"), θ=90° ("east"), θ=180° ("south"), or θ=270° ("west"). Obviously, any angles(s) in-between could be used. Using only one of the distance dimensions (FIG. 21) a few lines are generated which could be the potential position of the source. When a second distance dimension is added (FIG. 22), a small number of potential positions are calculated. The addition of the third (FIG. 23) and fourth (FIG. 24) displacement dimensions reduce the number of potential positions for the source. Ideally, only one potential position would remain; however, it is certainly possible that a couple of positions may exist. If multiple potential positions exist, the data from dead reckoning system can be used. Alternatively, if all other mechanisms for determining the position fail, it is likely that the position will be the one closest to the last confirmed position, especially if the position is determined several times a second. As more sensor positions and angles are taken, this is a less likely situation.

In an alternative embodiment, a map of the structure is generated without the source being tied to a method of knowing the initial location. In this case, the base station computer continuously receives data from the sources(s) and tries to generate a "best fit" for how the data can be placed. This algorithm is simplified by recalling that a position (target) reading cannot be taken too far from the previous reading. While this system may be computationally intensive, the system would eventually piece together enough of the position data, that position based on the map becomes possible.

In yet an alternative embodiment, the method for measuring the distance uses a laser generated grid (FIG. 25) and a frame grabber. As shown in FIG. 28, the size of the grid squares can be used to determine distance, the angle of the squares (FIG. 26) can be used to calculate within digital camera or an analog camera with a frame grabber the angle of the wall relative to the position of the source. Furthermore, the size of the grid can be used to determine the distance from the source to the target (FIG. 27). The closer the target is to the source, the smaller the target appears (FIG. 29) in a view-finder set to a fixed distance. As the target is further away, the size of the grid becomes larger (FIG. 30). The basic principle behind this system is that an image plane (for example video camera) is established such that at a distance of 10 meters ($d_x$) the total size of the image is 5 centimeters square (h). Using Equation 20, the image then sweeps through an angle, $\theta_1$, =0.28 degrees or 0.005 radians.

Equation 19:

$$\frac{h/2}{d} = \tan\left(\frac{\phi}{2}\right) \quad \text{or:}$$

Equation 20:

$$\phi = 2 \times \tan^{-1}\left(\frac{h/2}{d}\right)$$

If, at this same distance ($d_1$), the size of the grid is designed to be exactly half the image plane (2.5 cm in this example), then the angle of the laser image's sweep is $\theta_1$=0.0025 radians or 0.14 degrees. This system then produces a linear relationship where if the laser grid takes the entire image plane (whose focal plane does not change in relation to the distance to the target), then the target is half the focal plane distance away (in this case 5 meters). If the laser image takes only a quarter of the image plane, then the target is twice the focal distance away, or 20 meters. Other relationships using these angles can also be developed for determining the distance to the target.

Figure 31:
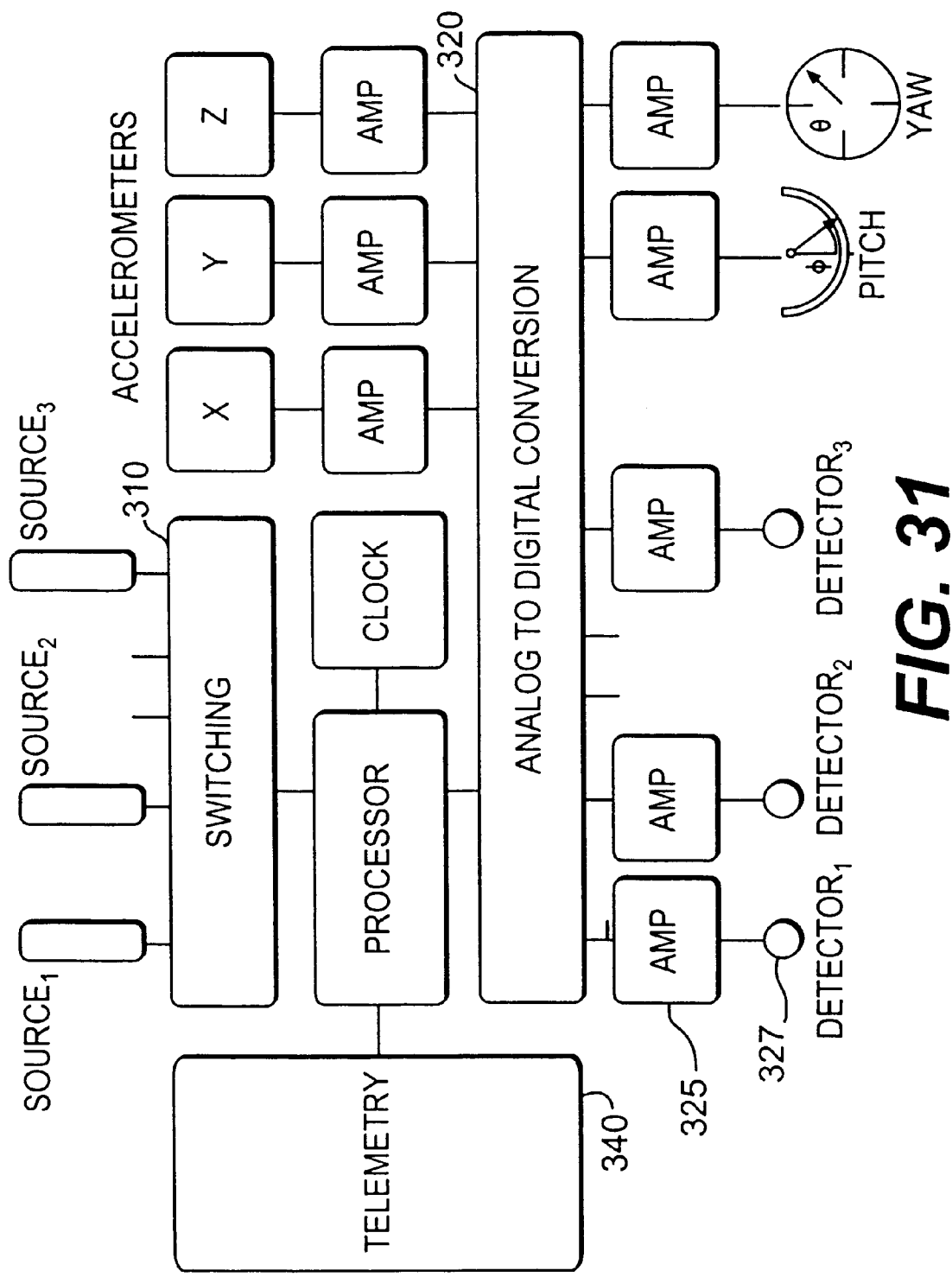
FIG. 31 is an electronic signal processing system according to one embodiment of the present invention.

The electronic processing required for the operation of this alternative system is divided into the following subsystems (FIG. 31). The first is the switching subsystem 310 required to turn the distance measuring source(s) on an off. The second is a subsystem 320 to convert the analog data from a variety of sensors into digital data for the processor to operate. In general, a series of signal amplifiers 325 will be required to boost the signal strength of the sensors to levels suitable for analog to digital (A/D) conversion. The analog sensors include detectors 327 for each distance measuring source, devices for measuring the pitch and yaw of the detectors, and accelerometers for monitoring movement in each of the three ordinal axis (forward/back, left/right, up/down). The addition of a telemetry component 340 is used to communicate the map and position data back to a central base station.

Figure 32:
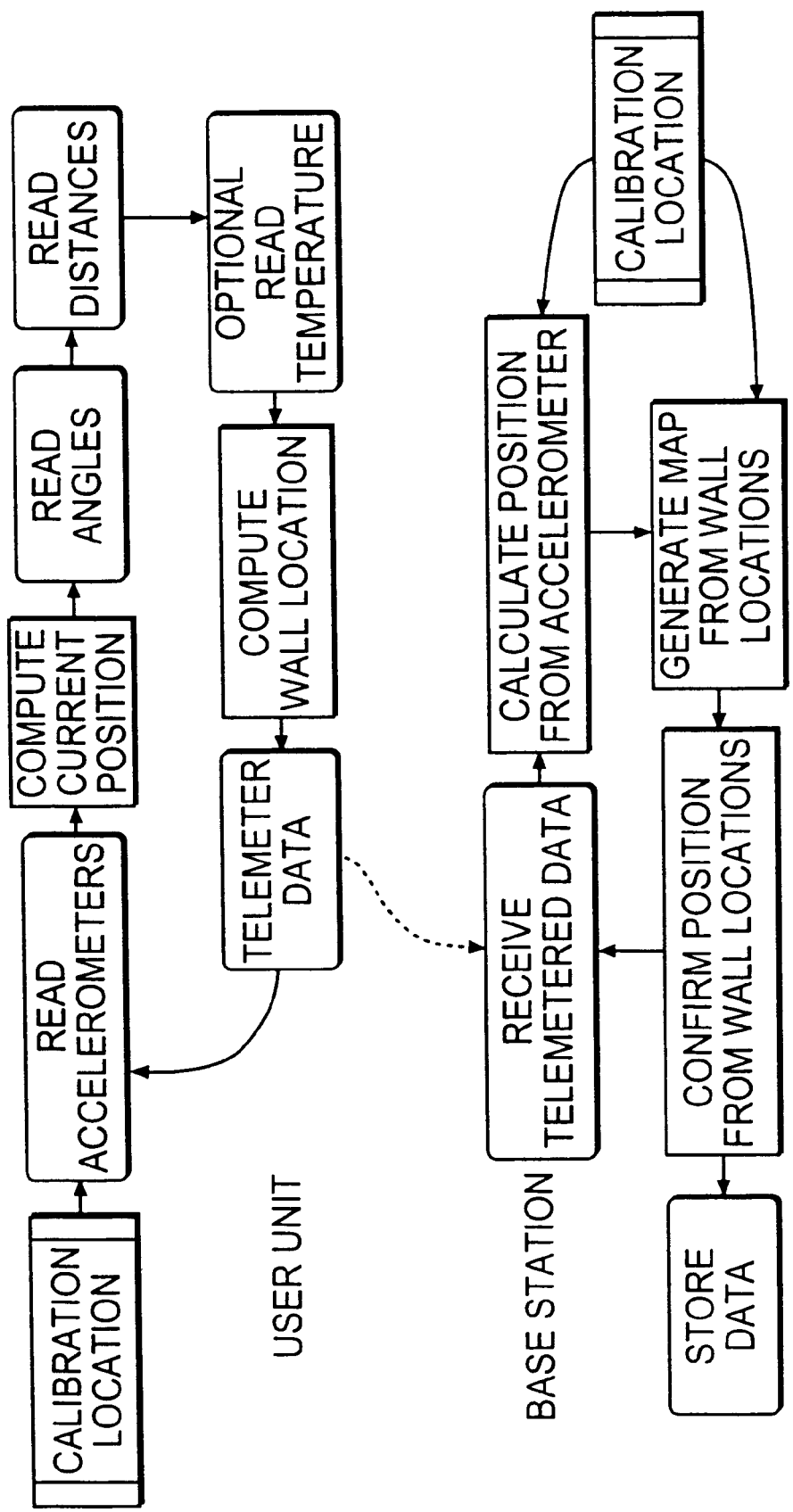
FIG. 32 is a flow diagram for operating a signal processing system according to one embodiment of the present invention.

The general flow of processing for this system is described in FIG. 32 below and by the following process:

Step Process

1. Initially the system is calibrated so that the dead reckoning system knows its starting position. This may be done by starting at a fixed location or by using some other location system such as a Global Positioning System (GPS) to derive the starting point.
2. All movement of the source will be registered through the accelerometers. The accuracy of the dead reckoning position is dependent upon the sampling frequency of the accelerometer sensors.
3. Once the data from the accelerometers have been read by the analog to digital conversion system, the velocity vector (velocity in each axis) can be calculated, and from this, the displacement vector (displacement in each axis) is calculated. This will provide the relative position of the source to the calibration point and previous measurement points.
4. Measurements are taken for the orientation (pitch and yaw angles) of the source.
5. The distance measuring system(s) are then used to calculate the distance to the targets.
6. In special cases of this system, not only will the system determine the distance to the target, but may also be able to calculate the target temperature.
7. The distance and orientation information is then used to calculate the position of the target(s) relative to the source.

8. All of this information is then communicated to the base station for recording and integration. The data communicated are the values acquired by the sensors (accelerometer, orientation, and distance data).

9. Finally, the system returns to measuring the accelerometers to calculate the-newest (current) position of the source as it moves throughout the structure.

Step Process

1. Upon receiving information from the user unit(s), the base station calculates a dead reckoning position for the source based upon the source's accelerometer data.

2. Using the orientation and distance information (relative to the source position), generate the connected dot-to-dot map. Data from multiple sources are integrated. Data from the current iteration is added to previous iterations of the data. This is continuously updated over time.

3. Using the distance and orientation data, confirm the dead reckoning-position based upon the most recent iteration of the structure's map.

4. The data is stored for record keeping and for later analysis and training.

5. The process repeats as more data is received through telemetry.

When a laser is used for measuring the distance to a wall, it is possible, by looking at changes in the returned reflection, to determine the temperature of the target (wall). Systems employing this technique are commercially available for sensing the temperature of a distant object without the use of a direct contact temperature probe. However, if this technique is used on out dot-to-dot maps, we learn the temperature of each of these locations, and the map can be modified to show temperature gradients throughout the nap. Furthermore, as the source(s) continue to gather data, the thermal data would also be updated, providing both a current temperature for that location, as well as a trend for the temperature (increasing, decreasing, remaining steady).

Overall system this is analogous to generating a five dimensional data space, the first three dimensions are the ordinal axes (up/down, left/right, forward/back). A dimension for temperatures, gas concentrations, and subject physiologic status is then added. Finally a dimension for changes (in temperature, structure, and the position of the sources) over time is added. This data, recorded at the base station, can be re-played after the event to gain valuable insight to the fire's behavior, and to be used in training to improve overall fire response. This system can also be used to assist in fire investigation for where a fire might have started and how it spread over the course of fighting it, or how the actions of the fire fighters changed the structure.

Figure 33:
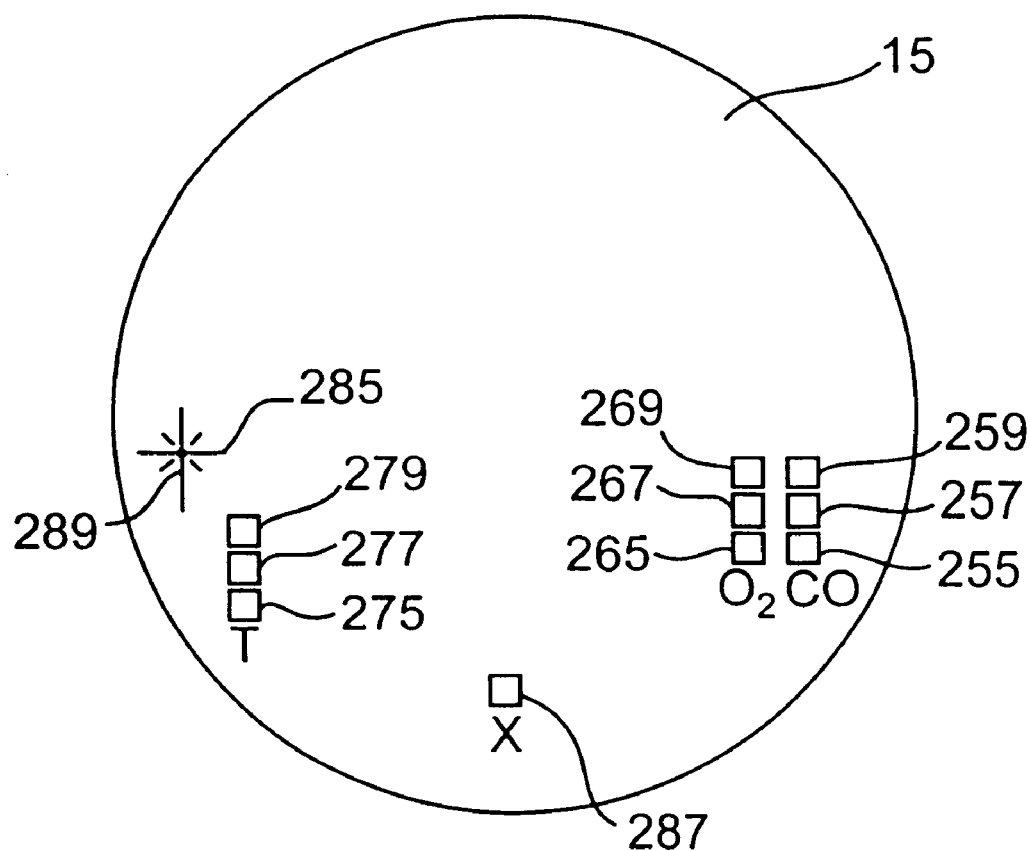
FIG. 33 is a representation of the sensor display of a mask for an SCBA according to one embodiment of the present invention.

In FIG. 3, sensors 20, 22, 26, 28, 30 and the position display system 200 on the mask 100 are wired to a transmitter 14 attached to the source of bottled oxygen in FIG. 2. Alternatively, the transmitter could be attached to a helmet or the SCBA mask. The transmitter includes a self-contained power source for powering both the sensors and the transmitter/receiver. The sensors and position display system are also connected to individual display units attached to the clear shield 15 of the mask 100. The display units are color coded (e.g., red, yellow and green) Lids that indicate simple safety levels associated with sensor data (i.e., carbon monoxide or oxygen pressure). These display units are shown in FIG. 33. The carbon monoxide (CO) display includes red LED 255, yellow LED 257 and green LED 259. Similarly, an oxygen saturation sensor display incorporates LED's 265, 267 and 269 and temperature display incorporates LED's 275, 277 and 279.

The mask 15 also incorporates an LED 287 that indicates whether or not the transmitter receiver is operational. In this way, the mask wearer knows that his physiological condition is being monitored. The mask 15 also incorporates a directional finder LED 285 and a transmitter LED that indicate to the individual a direction, forward, reverse, left or right (color coded). The directional finder 285 incorporates a red LED 289 which when "on" indicates to the individual wearing the mask that the base station is instructing the wearer to get to safety. The directional indicators lead the wearer to safety by essentially directing them through the map that has already been created in the base station by the position sensor system.

The transmitter receiver transmits a RF signal containing data for the sensors to a base station. The base station incorporates a processor that monitors the ongoing physiologic sensor data from individual personnel and compares that data with baseline data known about each individual person wearing the SCBA and compares that data with an ongoing history under the particular environmental conditions. In particular, the baseline data for each individual includes expected baseline data for an individual under normal physical stress, such as, exercise or working in a typical hazardous environment. This baseline data is updated with the actual monitoring data of each individual as that individual works under the hazardous conditions. In this way, the processing system can discriminate between normal "stress" and stress that may be hazardous to an individual in the circumstance.

Figure 34:
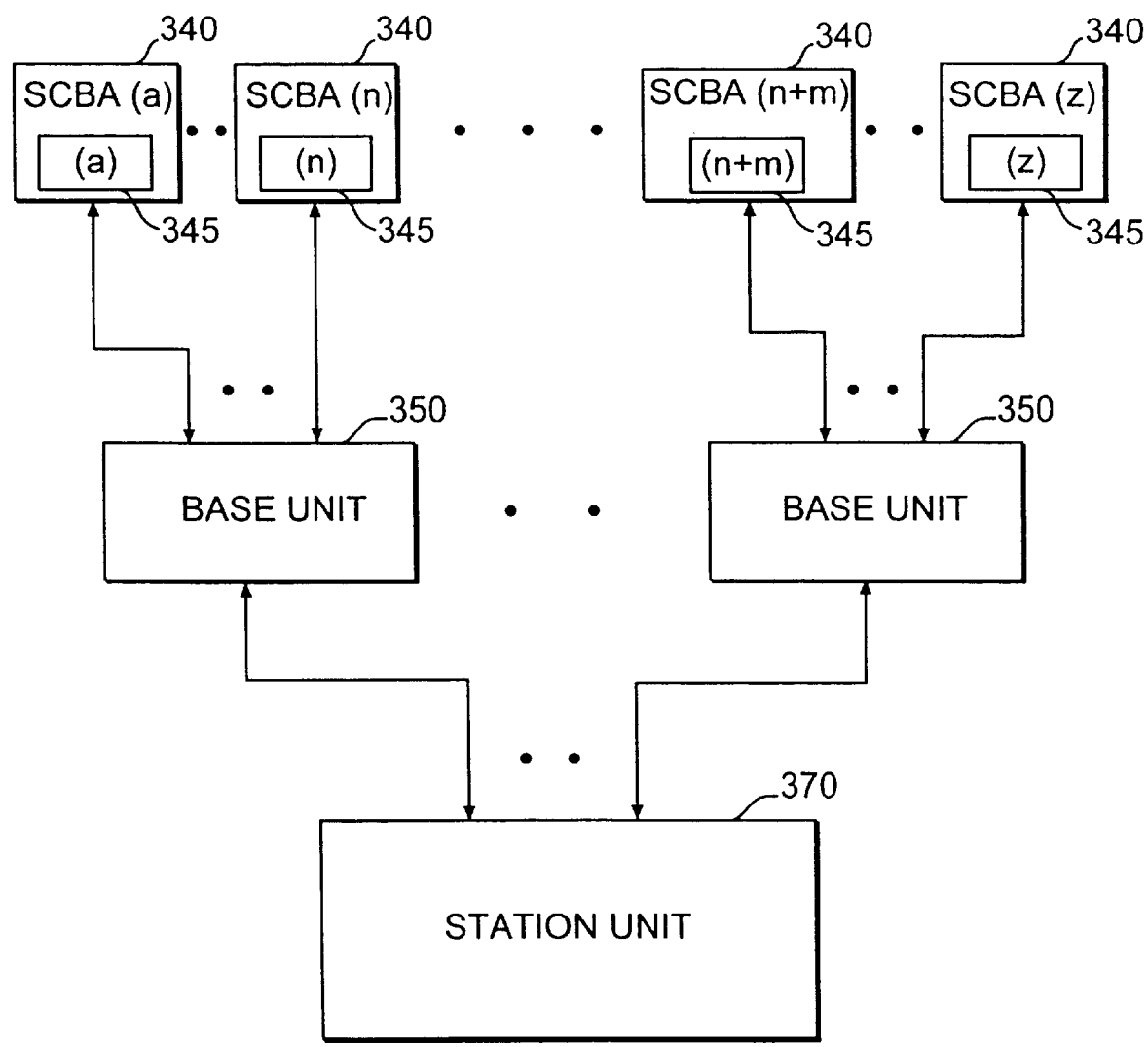
FIG. 34 is a schematic representation of a processing system for monitoring personnel according to one embodiment of the present invention.

FIG. 34 illustrates the network architecture of a processing system for analyzing the sensor data according to one embodiment of the present. In particular, a plurality of SCBA units 340 (A through E) each incorporate a processor/transmitter system 345. The processor/transmitter 345 analyzes the data from the sensors incorporated in the SCBA mask and creates a visual display on the mask indicating the status of the user. The processor/transmitter 345 also transmits the sensor information (including physiologic and location information) to one of a series of base units 350. Each base unit 350 processes the data from a plurality of SCBA units and is able to monitor the status of teams of people. Each base unit is also able to retrieve individual data concerning particular personnel from a central station unit 370 and transmit that data to the processor/transmitter 345. The processor/transmitter 345 then incorporates the individual data into its analysis of the physiologic or location status of the user.

For example, the station unit 370 may store data on the heart rate of a particular person and structural data on a specific building. The heart rate data may be used by the processor/transmitter 245 to modify the status displayed to the user as physical exertion is increased. The base unit 350 may also evaluate the location of the user through the sensor data and compare it to map data and structural data retrieved from the station unit 370. When there appears to be a dangerous condition, the base unit will then signal the SCBA unit. The processor/transmitter 345 would then indicate to the user that the user should evacuate the area.

Figure 35:
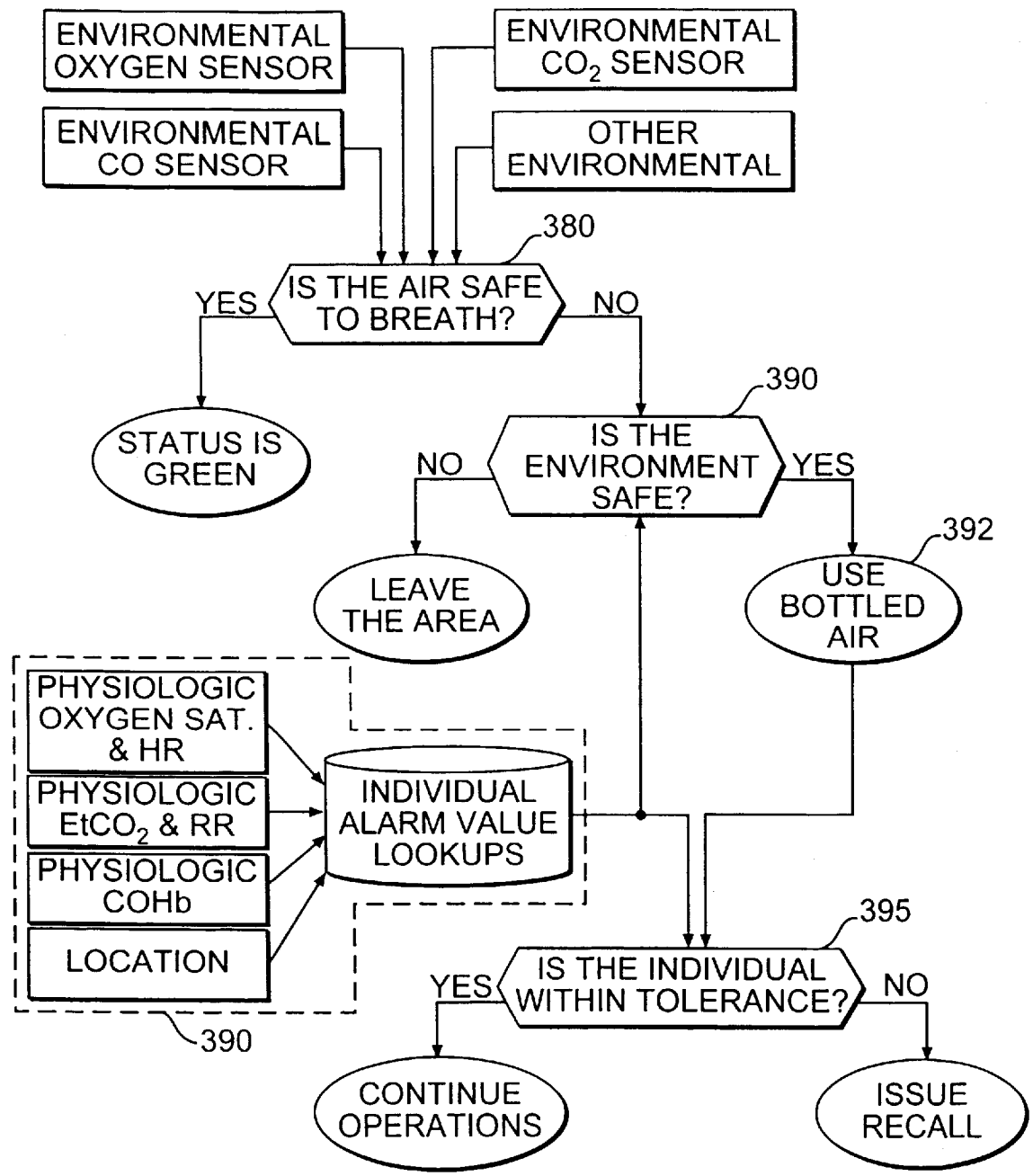
FIG. 35 is a flow diagram for operating the processor/transmitter of the SCBA according to one embodiment of the present invention.

The processor/transmitter 345 operates according to a flow diagram illustrated in FIG. 35. Specifically, environmental and location sensor information is collected by the SCBA sensor system. The processor/transmitter 345 initially determines whether the ambient air is safe to breath (380). If so, this status is indicated to the user. If not, the processor/transmitter determines whether the environment (390) is safe based on the environmental and location data. The location data may come from the base unit as illustrated by 390. If the environment is not safe, the user is switched to bottled air (392). While the user is on bottled air, the sensor and location information is used to determine whether the individual exceeds individual tolerance limits 395.

The physiologic system described above has been particularly described with respect to hazardous environment monitoring of personnel. This system, however, is adaptable to ideal environments in which personnel are nevertheless operating under stressful conditions and/or undergoing substantial physical exertion. Particular examples include monitoring athletes during competition. Specifically, the carbon monoxide and oxygen sensor systems are incorporated within a football or hockey player's helmet or other existing equipment (such as a headband or sweatband worn on the wrist) and also coupled to base and station units through processor/transmitter units (also incorporated into a player's equipment) to monitor the exertion of a player while that player is in competition. Base station analysis is then available to indicate to a coach which players are undergoing fatigue or other problems which may interfere with their performance. Other applications include the use of the sensor systems in military applications wherein sensor and location systems are incorporated into helmet systems and transmitted to base and/or station units. In all these applications, the individual exertion and/or location of personnel can be individually monitored on a real time basis through the sensor processing system.

While this invention has been described and illustrated with respect to specific plural embodiments thereof, it will be understood by those of skill in the art that various changes in the detail may be made without departing from the spirit, scope and teaching of the invention.

We claim:

1. A control system, comprising
    a plurality of breathing apparatii, each of said plurality of breathing apparatii having a source of gas;
        a face mask connected to said source of gas wherein gas is passed from said source of gas through said face mask;
        a first sensor mounted on said face mask wherein said first sensor detects an amount of exhaled carbon dioxide and produces a first data signal indicative thereof;
        a second sensor attached to said face mask wherein said second sensor detects an amount of carbon monoxide in a user's blood when wearing said face mask and produces a second data signal indicative thereof;
        a third sensor attached to said face mask wherein said third sensor detects an amount of oxygen in the user's blood when wearing said face mask and produces a third data signal indicative thereof;
        a processor connected to said first, second and third sensors wherein said processor receives the first, second and third data signals from said first, second and third sensors, respectively, and creates at least one condition signal indicating a hazard condition wherein the condition signal is derived from the first, second and third data signals;
        a display attached to said face mask and receiving said condition signal wherein said display indicates to the user whether a hazard condition exists;
        a transmitter/receiver unit connected to said processor wherein said transmitter/receiver unit receives data from said processor and transmits said data to a base unit; and
    a plurality of base units, each of said plurality of base units:
        having a base processor and a storage unit for processing and storing data from a plurality of transmitter/receiver units;
        transmitting data to each of said transmitter/receiver units; and
        monitoring the status of said sensors in said breathing apparatus.

2. A control system, as in claim 1, further comprising:
    a station unit having a station processor and a storage unit wherein said station unit communicates with said plurality of base units.

3. The control system of claim 1, wherein said base processor has baseline data with which to compare said data and create an other condition signal indicating whether a hazard condition exists.

4. The control system of claim 1, wherein each of said plurality of breathing apparatii further comprises a fourth sensor mounted to said face mask wherein said fourth sensor monitors the external temperature.

5. The control system of claim 1, wherein each of said plurality of breathing apparatii further comprises a fourth sensor mounted to said face mask wherein said fourth sensor monitors cyanides.

6. The control system of claim 1, wherein each of said plurality of breathing apparatii further comprises:
    a position sensor system connected to said face mask, said position sensor system comprises a distance measurement system comprising:
        a light source that emits a beam of light upon receiving a source signal from said processor; and
        a light detector that detects the light emitted from said light source after the light reflects off an object, said light detector producing a detector signal for said processor, said processor calculating the distance between said object and said face mask.

7. The control system of claim 6, wherein said position sensor system further comprises a direction sensor system, said direction sensor system comprising:
    a magnetometer system capable of measuring the yaw of said light source, said magnetometer system producing a yaw signal; and
    a mercury switch capable of measuring the pitch of said light source, said mercury switch producing a pitch signal, said processor receiving said yaw and pitch signals and calculating the direction said face mask is traveling.

8. The control system of claim 7, wherein said transmitter/receiver unit sends the distance and direction data to one of said plurality of base units, said base unit producing a map of the surroundings of said corresponding face mask.

9. The control system of claim 8, wherein said base unit calculates the position of said face mask in relation to said map.

10. The control system of claim 9, wherein said base unit transmits the map and position data to said transmitter/receiver unit, wherein the map and position data is displayed on said display.

11. The control system of claim 10, wherein said base unit transmits position data for at least one other breathing apparatus to said transmitter/receiver unit, wherein the position data for said other breathing apparatus is displayed on said display.

12. The control system of claim 10, wherein said base unit transmits position data to a transmitter/receiver unit for one other breathing apparatus.

* * * * *